United States Patent [19] [11] 4,265,519
Pomerantzeff [45] May 5, 1981

[54] WIDE-ANGLE OPHTHALMOSCOPE

[75] Inventor: Oleg Pomerantzeff, Brookline, Mass.

[73] Assignee: Retina Foundation, Boston, Mass.

[21] Appl. No.: 292,150

[22] Filed: Sep. 25, 1972

[51] Int. Cl.³ .............................................. A61B 3/10
[52] U.S. Cl. ........................................ 351/16; 351/6; 351/7
[58] Field of Search ............................ 351/1, 6, 7, 16; 350/96 B, 175 GN, 45; 95/11 E, 11 M, 45; 354/62

[56] References Cited

U.S. PATENT DOCUMENTS

| 1,605,725 | 11/1926 | Herbert, Jr. | 351/7 |
| 2,959,099 | 11/1960 | Billard et al. | 350/45 UX |
| 3,001,441 | 9/1961 | Herbert | 351/16 |
| 3,630,602 | 12/1971 | Herbert | 351/16 |
| 3,770,342 | 11/1973 | Dudragne | 350/96 B X |
| 3,780,979 | 12/1973 | Guillebon | 351/7 X |

OTHER PUBLICATIONS

Oleg Pomerantzeff et al., "Design . . . Ophthalmoscope", Arch Ophthal, vol. 86, Oct. 1971, pp. 420–424.

Primary Examiner—Paul A. Sacher
Attorney, Agent, or Firm—Kenway & Jenney

[57] ABSTRACT

A wide-angle indirect ophthalmoscope that enables an operator to view the retina from the posterior pole to the equator as a single image. The ophthalmoscope has an observable field that can include the entire retina. The ophthalmoscope includes optical fibers built into a contact lens in a circular pattern. The fibers are connected to a light source to illuminate the retina, and the contact lens is utilized for observation. The fibers are maintained in a pre-determined fixed orientation in the lens to produce uniform illumination over the entire retina.

30 Claims, 7 Drawing Figures

WIDE-ANGLE OPHTHALMOSCOPE

The invention described herein was in part made in the course of work under a grant or award from the Department of Health, Education and Welfare.

BACKGROUND OF THE INVENTION

The present invention relates in general to instruments which are used to examine the interior of the eye and in particular to ophthalmoscopes, as they are often called.

Because an observation of the patient's retina is a prerequisite of a diagnosis, ophthalmoscopes play an important role in a clinical examination. However, since the time when ophthalmoscopy became part of every clinical examination, ophthalmologists have been anxious to improve the performance of ophthalmoscopes, and in particular they have been anxious to improve the field of view and the observable field that can be obtained with an ophthalmoscope. In connection with the foregoing, the field of view is the area of the fundus covered by the observer's eye in any given direction of observation, i.e., the area of the fundus that is seen as one view without scanning, and the observable field is the area of the fundus limited by a boundary beyond which the ophthalmoscope is unable to reach, i.e., the total area of the fundus that can be seen in several views by scanning. The effort that has been made to increase both of these fields has been continuous and somewhat successful.

Ophthalmoscopes are classified into two types or groups—direct ophthalmoscopes and indirect ophthalmoscopes. Direct ophthalmoscopes enable a field of view not larger than 12° of arc, which corresponds to a relatively small area of the fundus (4 mm. in diameter) and only enable an observable field hardly reaching the equator. Direct ophthalmoscopes, however, enable a 15-power magnification of the field of view. Thus, although the direct ophthalmoscope only enables a field of view of barely 2 to 3 disk diameters, this instrument is employed when high magnification of that area is desired. In this regard, prior art indirect ophthalmoscopes only enable a three-power magnification of the field of view.

Because of the inability of direct ophthalmoscopes to provide a large field of view, indirect ophthalmoscopes are widely in use. One reason for the use of indirect ophthalmoscopes, besides the ability of this instrument to explore the peripheral retina more efficiently, is their larger field in view. In this regard, the indirect ophthalmoscope extends the field of view that can be provided to about 35° of arc, that is 8 to 10 disk diameters, and by moving the instrument to scan the patient's eye the observable field that results includes the ora serrata.

The parameter limiting the field of view in the indirect ophthalmoscope is the numerical aperture of the condensing lens. The recent improvement of the condensing lens by increasing its numerical aperture up to F/1 permits an increase in the field of view to approximately to 45° with a +20D lens. The numerical aperture F/1 is the approximate limit of the optical performance possible. A slight increase (55°) can still be gained with the +30D lens at the expense of loosing $\frac{1}{3}$ magnification.

A distinct disadvantage of all known ophthalmoscopes is that they do not permit a single view of the fundus from the posterior pole to the equator. In order to obtain such a view of the fundus to make accurate determinations of the diseased state, an ophthalmoscopist must scan this portion of the fundus and draw a map of what he sees as he views one area of the retina and then the next. A hand-drawn or photo map is the only image of the area of the retina from the posterior pole to the equator that the ophthalmoscopist has to work with.

The ideal ophthalmoscope or the ideal fundus camera should give a picture of the whole retina from the posterior pole to the ora serrata. Such a picture would eliminate the time consuming and inaccurate mapping of the fundus which is tiring for both the patient and the ophthalmologist. In accordance with one embodiment of the present invention, which includes clad fibers, such mapping is significantly reduced because the instrument enables a single view of the fundus from the posterior pole to the equator. In another embodiment of the invention, which includes "selfoc" fibers, a single view of the entire retina is possible.

Thus, the present invention is a wide-angle ophthalmoscope which includes fiber optic light guides for illuminating the retina. The light guides function in conjunction with a lens to provide a wide-angle view of the field which is uniformly illuminated by the fiber optic light guides.

An illuminator which includes fiber optics to illuminate the retina is disclosed in French Pat. No. 1.583.436 by Raymond André Dudragne.

The illuminator disclosed in this French patent, however, is not considered suitable because it provides only a very restricted field of observation and can produce reflections of the illuminating light which can blur the image of the retina. In addition, French Pat. No. 1.583.436 suffers from a serious deficiency in that this patent does not disclose the proper location of the ring of illuminating fibers, nor does it disclose the importance of the angle of inclination of the illuminating fibers. Furthermore, the French patent does not disclose the importance of wide-angle fibers.

In connection with the foregoing, an important aspect of the present invention is the location of the illuminating circular bundle of fibers, the inclination of the fibers at the contact point with the cornea and the numerical aperture of the fibers. These points are amplified below.

SUMMARY OF THE INVENTION

The deficiencies of the prior art ophthalmoscopes are significantly overcome by the ophthalmoscope of the present invention which is a wide-angle ophthalmoscope which includes a lens and an illuminating ring of optical fibers in a pre-determined orientation with the lens. In one embodiment of the invention, the optical fibers are wide-angle fibers with the index of refraction of the core and cladding of the fibers being selected to yield a high numerical aperture. The fibers are oriented within the lens so as to permit illumination of the entire retina and a single view of the retina from the posterior pole to the equator.

With a normal emmotropic eye, the instrument enables 2.5 magnification of the fundus from the posterior pole to the equator with up to 12 power magnification of a small area (3 disk diameter or 4 mm.) of the fundus.

By utilizing the so called "selfoc" fibers in place of clad fibers, an ophthalmoscope results which enables the viewer to see the entire retina from the posterior pole to the ora serrata.

The contact lens is composed of a central, mushroom-shaped piece and an external, ring-shaped piece. The foregoing construction is utilized to maintain the ring of optical fibers at a pre-determined inclination at the contact point with the cornea.

Accordingly, it is an object of the present invention to provide an ophthalmoscope which will uniformly illuminate the retina and provide a wide-angle view of the illuminated field.

A further object of the invention is to provide a wide-angle ophthalmoscope which will enable an operator to view the interior of the eye from the posterior pole to the ora serrata.

A further object of the invention is to provide an ophthalmoscope which includes a magnifying lens and a plurality of optical fibers with a high numerical aperture and which are oriented within the lens in a pre-determined position.

A further object of the invention is the provision of an ophthalmoscope which includes clad fibers with a relatively high numerical aperture which are located within a contact lens in a pre-determined position and which enables the operator to view a retina from the posterior pole to the equator in a single image.

A further object of the present invention is to provide an instrument which will enable the operator to both view a fundus as one picture and also permit magnified observation of a partial area of the fundus.

A further object of the present invention is to provide a fundus camera which includes a contact lens and clad fibers which have a relatively high numerical aperture with the fibers in a pre-determined position within the lens and which enables the operator to produce, in a single photograph, a picture of the retina from the posterior pole to the equator.

Still another object of the present invention is the provision of a fundus camera which includes selfoc fibers in a pre-determined position within a contact lens and which permits the operator to produce a single photograph which contains a picture of the entire retina from the posterior pole to the ora serrata.

DESCRIPTION OF THE PREFERRED EMBODIMENTS

At the outset, the invention is described in its broadest overall aspects with a more detailed description following.

Figure 1:
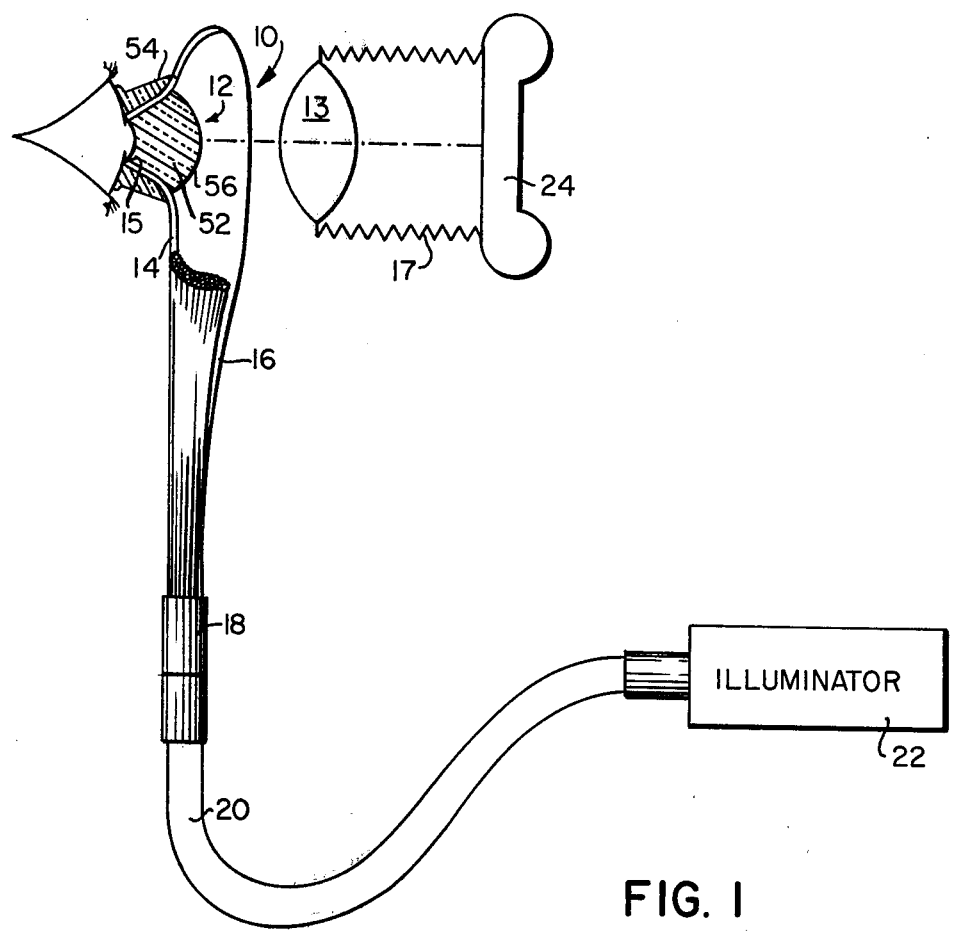
FIG. 1 is a schematic diagram showing the overall aspects of the ophthalmoscope of the present invention in an optical circuit with a camera.
Figure 2:
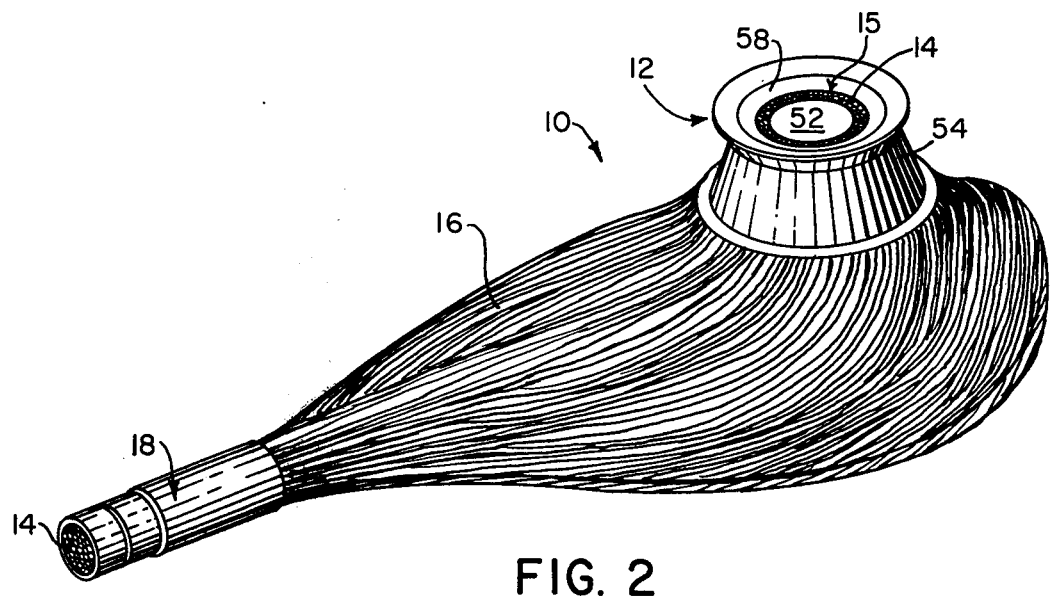
FIG. 2 is a perspective view of the ophthalmoscope of FIG. 1 with the protective covering material removed.

As is shown in FIGS. 1 and 2, the ophthalmoscope 10 of the present invention includes a contact lens 12 and a plurality of optical fibers 14. One end of each of the fibers 14 faces the patient's cornea when the ophthalmoscope is in use, and together the fibers 14 form a ring 15 within lens 12. Ring 15 forms a circular pattern of light when the instrument is in use.

As is shown in FIG. 1, the ophthalmoscope of the present invention is designed so that contact lens 12 contacts the patient's cornea when the instrument is in use. As is explained in more detail below, the fibers which form ring 15 contact the surface of the patient's cornea when lens 12 itself is positioned on a patient's cornea.

Optical fibers 14 extend through the viewing end of contact lens 12 whereupon they are protected by a covering 16. The fibers extend through covering 16 to a metal connector 18. Metal connector 18 is connected to a fiber optic cable 20 which in turn is plugged into a fiber optic illuminator 22. Thus, light from the illuminator 22 is conducted through cable 20 and into the ophthalmoscope for illumination of the patient's retina. For best results, it has been discovered that the optical fibers in cable 20 should be the same fibers as those used in the ophthalmoscope, i.e., fibers 14. The image of the retina is viewed through contact lens 12 and may be photographed with a camera 24. Camera 24 may be a conventional camera. Because of the wide field of view resulting from the use of the ophthalmoscope of the present invention, it is desirable to include a field lens as part of the optical train in camera 24 to condense this field.

For optimum results, the field lens should have an aperture equal to the cone containing the image of the retina which in most cases is f/1. Field lens 13 may be an aspheric lens or a system composed of as many as five lenses. In addition to having an aperture of f/1, the field lens 13 should be fairly wide (60 mm. radius). Any corrected lens, however, that has a radius of 60 mm. and an aperture of f/1 may be used as part of the optical train. In instances where the ophthalmoscope is used to simply view the retina without taking a photograph, the field lens may be hand held by the physician. When the ophthalmoscope is used as part of a fundus camera, as is shown in FIG. 1, it is advantageous to attach a field lens 13 to the camera 24 by a bellows 17.

The ophthalmoscope of the present invention is constructed not only to be compatible with the organs in the eye, but also to utilize such organs to maximum advantage. For example, the field of view of a normal individual extends temporally to at least 90 degrees of arc. This means that the rays emitted toward the observer's pupil by all the points in a field of about 180 degrees of arc pass through an undilated pupil and reach points in the observer's retina. Rays reaching the retina from the nasal portion of the field fall on an area of the retina that is not photosensitive. Inversely, if the retina is illuminated, its points emit rays which when passing through an undilated pupil, contain the aerial image of the whole retina and form a solid angle of about 180 degrees of arc. Thus, a small-pupil ophthalmoscope with an optimally corrected condensing lens permits observation of the peripheral retina through an undilated pupil. However, to view the entire retina in a single image, the entire retina must be illuminated without producing bothersome reflections, and the solid angle containing the aerial image of the fundus must be condensed to permit its simultaneous projection into the observer's retina.

Figure 3:
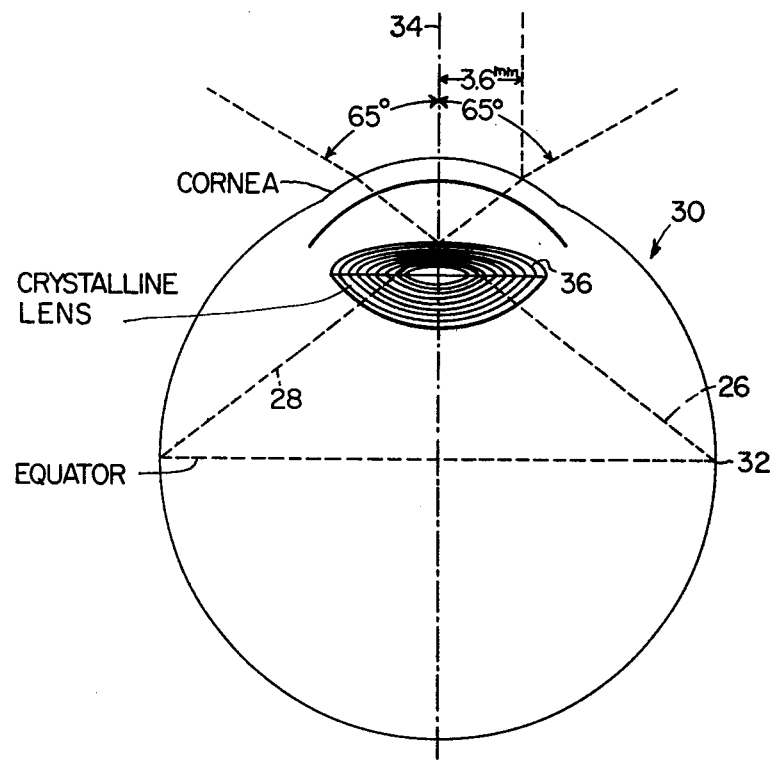
FIG. 3 is a model of a human eye illustrating the importance of the pre-determined orientation of fibers within the lens in accordance with the present invention.

In order to illuminate the entire retina without reflections and to condense the image of the fundus, fibers 14 are maintained in a pre-determined orientation within lens 12. By referring to FIG. 3, which shows a model of an average human eye, the importance of this pre-determined orientation is evident. As is shown in FIG. 3, two rays 26 and 28 extend through an eye 30 from both the nine o'clock and three o'clock ends of the equator. Both rays 26 and 28 pass through a one millimeter pupil located in the pupillery plan of eye 30 on its axis. The two rays 26 and 28, in the air, limit a solid angle which contains the image of the whole posterior hemisphere of the fundus that can be seen from outside the pupil. Thus, the limiting rays 26 and 28 emerge at 3.6 mms. on both sides of the axis 34. In view of this fact, the central area of the cornea extending at least up to 3.6 mms. from the center should be kept unobstructed by the fibers 14 when the ophthalmoscope is in use. By designing the ophthalmoscope so that fibers 14 stay clear of this central area of the cornea, an image of the entire retina can be viewed without obstructions. At this point, it should also be noted that the 65° half angle aperture of the solid angle contains the image.

In connection with the model shown in FIG. 3, at this point it should be emphasized that eye 30 represents a model of an average emmotropic adult eye. Thus, any dimensions given in the specification in connection with eye 30 represent the dimensions of such an average eye. The significance of the foregoing is that the parameters of the ophthalmoscope of the present invention are optimized to be compatible with the model eye 30. However, as will be apparent to those skilled in this art, the parameters of the ophthalmoscope can be varied so that the instrument can be utilized on a patient whose eyes deviate from this model. A case where such deviation is noteworthy is the case of small children. However, from the present specification, one skilled in the art is provided with all the information necessary to make whatever corrections are necessary to provide an ophthalmoscope in accordance with the general concepts of the present invention which can be effectively utilized to examine and photograph the retinas of children or any other patients having eyes which deviate from the model eye 30.

In connection with reflections, since fibers 14 are in contact with the cornea, when the ophthalmoscope is in use, the front corneal surface of eye 30 produces no reflections which interfere with observation. There are, however, annoying reflections from the front and back surfaces of the crystalline lens 36.

Figure 4:
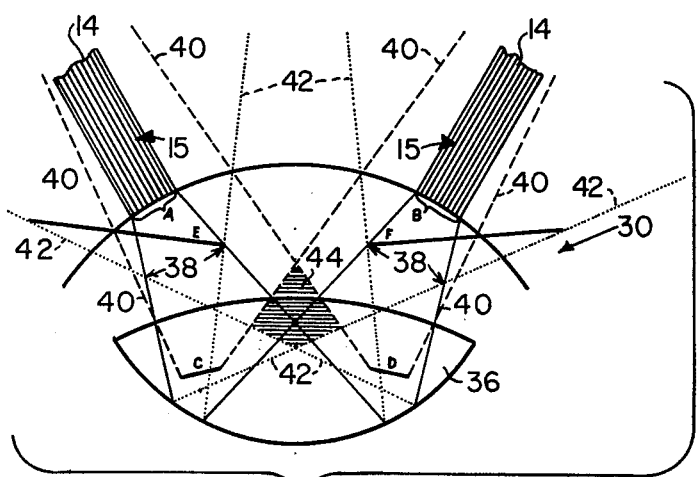
FIG. 4 is a diagram illustrating the reflection by the crystalline lens of an eye of light transmitted through a ring of fibers.

FIG. 4 shows a meridional section of the optical system composed of the eye 30 and ring 15 formed by fibers 14. It should be noted that in FIG. 4, as well as in other figures of the drawing, the size of fibers 14 is greatly exaggerated. Two points on ring 15 are labeled A and B. The corresponding limits of the illuminating beam are indicated by thin solid lines 38. The images of A and B formed by the front surface of the crystalline lens 36 (which is considered as a mirror) are labeled C and D. The dashed lines 40 starting from images C and D show the beams carrying the reflections. The reflections from A and B formed by the back surface of the crystalline lens 36 are labeled E and F. Corresponding beams carrying the reflections are indicated by dotted lines 42 starting from E and F. As is apparent from FIG. 4, to prevent the reflections from entering the observer's eye, the only place where the entrance pupil of the observation system can be located is the cross-hatched area 44.

Figure 5:
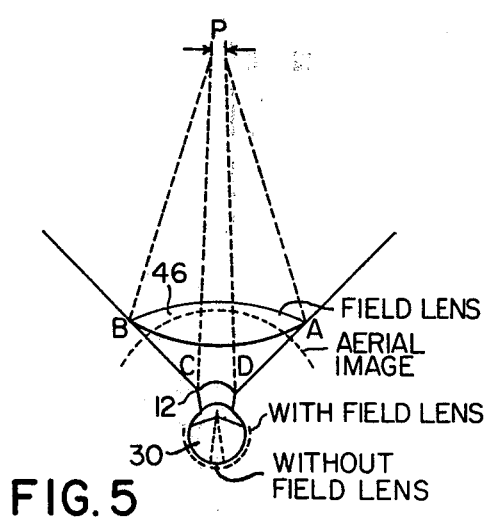
FIG. 5 is a diagram of a complete system showing how an entire image is seen by an observer through a field lens.

FIG. 5 shows that an observer placed at a reading distance from the aerial image of the fundus sees no more than a very small portion of it. To obtain a wide view of the retina, a field lens 46 is necessary. Thus, FIG. 5 is a complete diagram of a system for viewing an image of a retina from the posterior pole to the equator. FIG. 5 includes patient's eye 30, contact lens 12, field lens 46 and the observer's pupil labeled P. In FIG. 5, lines CP and DP limit a beam entering the observer's eye without a field lens. Lines AP and BP show how an entire image is seen by an observer with the use of a field lens 46. As has been set forth above, the field lens may be hand held by the observer or in the case of a fundus camera, the field lens may be attached to the camera by a bellows so as to be adjustably positioned between the camera and the patient's pupil.

As is set forth above, the entrance pupil of the observation system must be located in a relatively small area (crosshatched area 44 of FIG. 4) of the meridional section of the patient's eye. The entrance pupil of the observation system is the image of the observer's pupil formed by the entire observation system, i.e., the field lens 46, the contact lens 12 and the optical system of the patient's eye. The parameters: radius, thickness and refractive index, of the contact lens 12 are adjusted in order to condense and locate the image of the fundus. The parameters available for correcting and locating the image of the observer's pupil are those of the field lens. It should be noted, however, that the choice of parameters for field lens 46 is well within the skill of those in this art.

In addition to the fact that the location of the fibers 14 is critical in that the fibers must be placed on the patient's cornea so as not to obstruct the observation system, the correct placement of fibers 14 is also critical if optimum illumination of the retina is desired.

Figure 6:
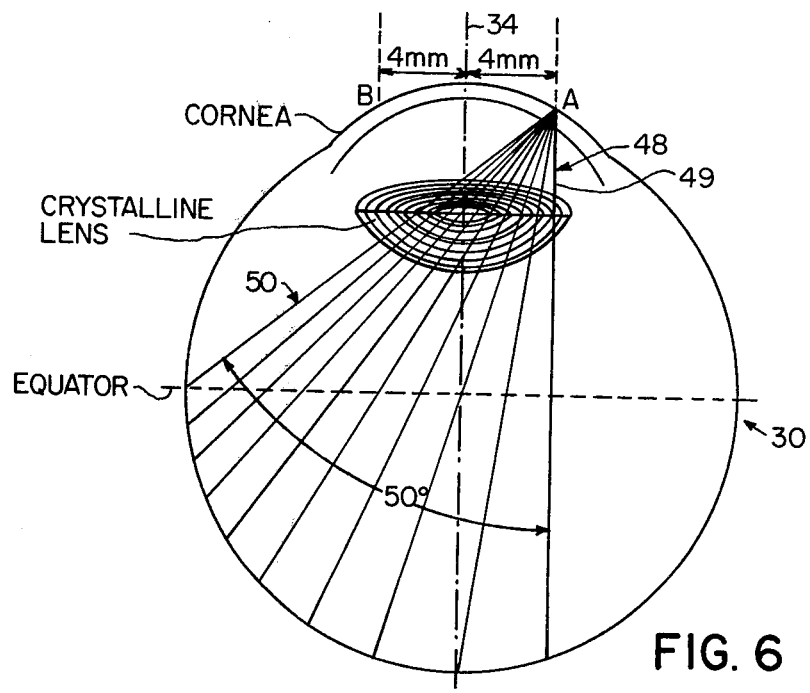
FIG. 6 shows the pattern of a bundle of rays passing through a human eye.

In connection with the foregoing, FIG. 6 shows eye 30 with a bundle of rays 48 passing through the crystalline lens of the eye. The first limiting ray 49 of the bundle 48 strikes a point located on the retina between five and six o'clock. The other limiting ray 50 strikes the equator. As is shown in FIG. 6, all rays in bundle 48 enter the eye through the cornea at a single point A located 4 mms. from the optical axis 34. Since bundle of rays 48 represent a cone of light, a symmetrical cone of light entering the cornea from a point B which is symmetrical of A about axis 34 would illuminate the whole posterior hemisphere of the globe. As is apparent with such an arrangement, there is some overlap of light at the posterior pole which is desirable to compensate for the overlap of the light from adjacent fibers.

As is also shown in FIG. 6, to achieve the foregoing illumination, the angular aperture of the bundle of light rays 48 in ocular media of the eye must be 50° of an arc. In connection with this point, it should be noted that conventional optical fibers have an angular aperture of 70° of arc, in air, which is reduced to about 40° in an eye. Thus, in addition to the requirement that fibers 14 be located at the 4 mm. separation from the axis 34, wide-angle or high numerical aperture fibers must be used to produce a cone of light which will travel with an angular aperture greater than 50° of an arc in the ocular media of an eye.

In addition, the inclination of the fibers at the contact point with the cornea must coincide with the axis of the cone which is making an angle of 30° of arc with axis 34 of eye 30. In connection with the foregoing and as is shown in FIG. 3, the half aperture of the solid angle containing the image of the fundus is 65°. Any fibers that protrude inside this solid angle of the image will obstruct part of the field.

In view of the foregoing, in accordance with the present invention, fibers 14 are bent inside contact lens 12 in order to prevent fibers 14 from intruding into the solid angle of the image. Thus, the inner radius of the ring of fibers 14 is 4 mm. and the angle of inclination of the fibers in the lens 12 as they contact the cornea is 30°.

In connection with the radius of ring 15, it should be noted that the ring can have an inside radius as small as 3.6 mm. The width of the ring is preferably about 1 mm.

If the radius is increased and the inclination made more oblique, the posterior pole becomes dark. If the fibers are not bent, but continue in a straight line with the slope required for the illumination of the posterior pole, they protrude into the solid angle containing the image of the retina.

As is set forth above, the ophthalmoscope of the present invention employs optical fibers 14 for illuminating the retina. Fibers 14 operate on the principle of total internal reflection. This principle is so well known that it requires only a brief description. A transparent elongated smooth surfaced body of higher refractive index than its surroundings can transmit light applied to one end so that it emerges with little loss at the other end, due to total internal reflection from its surfaces, of light rays divergent from the longitudinal axis of the body. To produce total internal reflection within each fiber, each fiber is formed of a central glass core surrounded by a thin sheath or clading of glass having a lower refractive index than the core. Although glass fibers are preferred, light guiding fibers may be formed of transparent plastics. However, the construction of light guiding fibers from either glass or plastic is well within the skill of those in this art.

Since fibers 14 do not transmit an image, but only are used for illuminating the retina, fibers 14 are not arranged to be coherent.

As is set forth above, one important embodiment of the ophthalmoscope of the present invention utilizes wide-angle clad fibers. A suitable wide-angle fiber is one with a numerical aperture (N.A.) of 0.86. Such a fiber has a total effective acceptance angle of 82°. A suitable refractive index relationship for a clad fiber, which can be utilized to produce a numerical aperture of 0.86, includes a core glass with a refractive index of 1.62 and a cladding formed from a second glass having a refractive index of 1.52. Fibers 14 preferably have a diameter of 0.002 inches or 2 mils. Suitable wide-angle fibers can be purchased from Applied Fiber Optics, Inc., 46 River Street, Southbridge, Mass. Of course, as is apparent, fibers with numerical apertures higher than 0.86 can be utilized in accordance with the present invention. However, fibers with a numerical aperture of 0.86 and a total effective acceptance angle of 82° have been found to be satisfactory. Furthermore, "selfoc" fibers as they are called can be utilized in place of clad fibers.

The "selfoc" fiber is a recent addition to the fiber optics technology. As has been explained above, total internal reflection in a fiber is normally achieved by cladding a core of a fiber of a pre-determined refractive index with a cladding having a lower refractive index than the core. In the case of selfoc fibers, a refractive index gradient is formed in the fibers. Thus, the refractive index of the fiber is highest at its axis and gradually decreases to a minimum at its periphery. Selfoc fibers, however, do not emit light in a divergent beam but actually focus the light. Because selfoc fibers focus light, when these fibers are utilized in the ophthalmoscope of the present invention, the reflections of light emitted by these fibers are modified by locating its focus close to the crystalline lens. Thus, the entrance pupil of the observation system does not have to be restricted to the cross-hatched area 44 of FIG. 4. Thus, when selfoc fibers are used, the viewer can observe the entire retina of a patient from the posterior pole to the ora serrata.

From the foregoing, it is apparent, that the orientation of fibers 14 in conjunction with lens 12 is critical. Furthermore, the angle at which light traveling through the fibers strikes the cornea is also critical.

Figure 7:
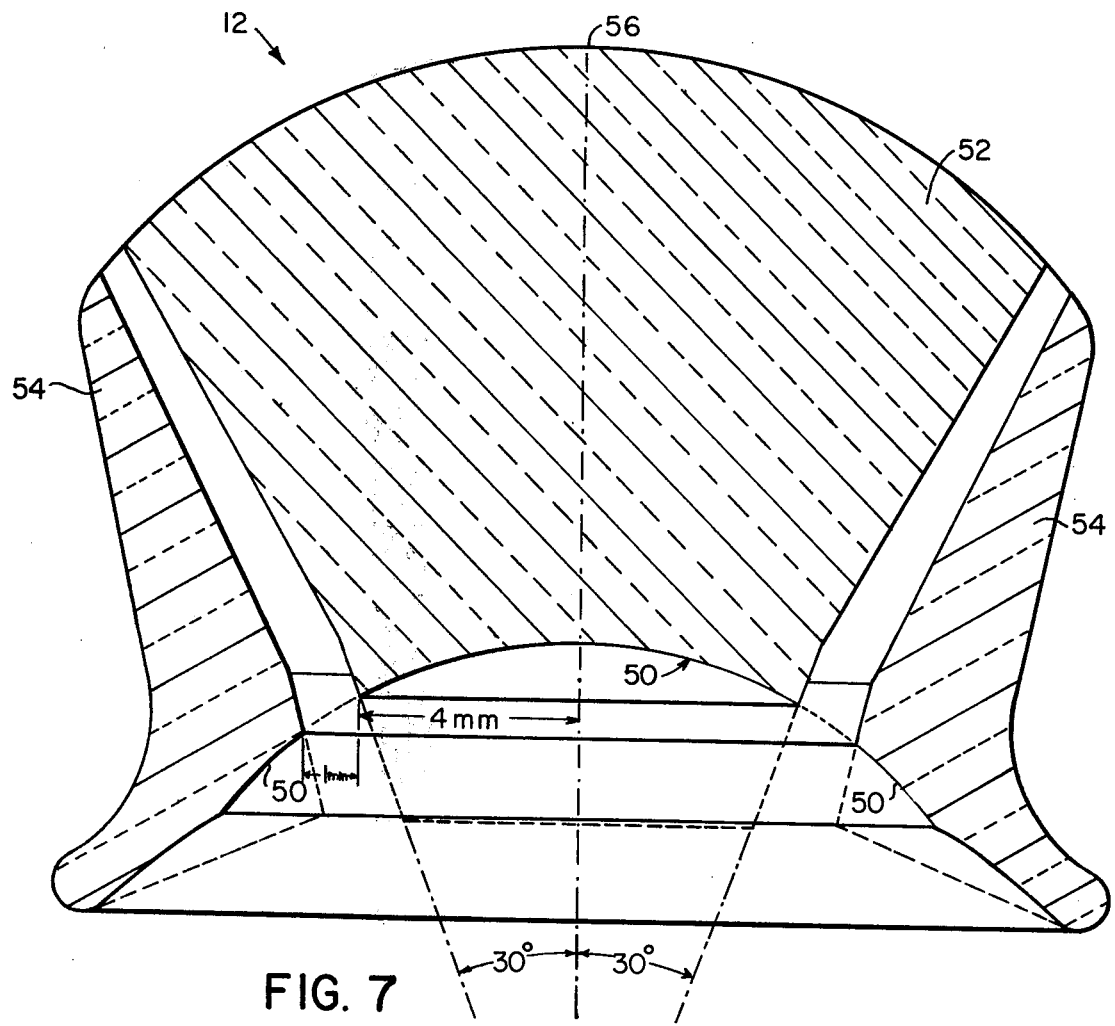
FIG. 7 is a cross-sectional view of the components which make up the lens of the ophthalmoscope of the present invention.

To achieve the proper relationship between lens 12 and fibers 14, lens 12 is made in two parts, and the fibers 14 are sandwiched between the two parts. As is shown in FIG. 7, lens 12 is inclusive of two parts, a central mushroom member 52 and an external ring 54.

During construction of the ophthalmoscope, fibers 14 are suspended around the mushroom member 52 and are evenly distributed on the ring 54. The mushroom member 52 and rings 54 are then forced together with fibers 14 between them. An epoxy is injected in the space between mushroom member 52 and ring 54. When the epoxy has cured inside the lens, the fibers outside the lens are arranged in a convenient shape and covered with epoxy.

The epoxy not only cements mushroom member 52 and ring 54 together, but also maintains the fibers 14 at their predetermined position and protects the fibers from damage when the ophthalmoscope is in use. Various resins have been found satisfactory for making ophthalmoscopes in accordance with the present invention. One such resin is prepared by Applied Fiber Optics, 46 River Street, Southbridge, Mass., under their designation AFO-21B-13. Another epoxy which can be utilized in the ophthalmoscope of the present invention is sold by the Shell Oil Company under their trade name Epon-828. It should be understood, however, that the purpose of the epoxy is to cement the lens components together and protect fibers 14 from breakage. Thus, other materials which performs the foregoing function are usable in accordance with the present invention.

As is set forth above, the image of the fundus formed by the optical system of the eye is contained in a solid angle of about 130° of arc with its summit in the subject's pupil. However, with lens 12 formed of a glass with a refracted index of 1.96, or higher, and with the foregoing configuration, the solid angle containing the aerial image of the retina is reduced to 90° of arc and the aerial image of the fundus is formed at about 50 mm. from the pole of the contact lens. Thus, in order to condense the image into this smaller solid angle, glass of a very high refractive index (at least 1.96) is employed for contact lens 12. A suitable glass for forming both mushroom member 52 and ring 54 of contact lens 12 is sold by Jenaer Glaswerk Schott & Gen., Mainz, West Germany, under their designation LaSF 6-961349. This glass has a refractive index ($n_d$) of 1.96052.

After the fibers are cemented in place between the mushroom member 52 and the ring 54 of lens 12, the lens is ground and polished to the configuration shown by the solid lines of FIG. 7.

When fully fabricated, lens 12 has an outer convex surface 56 with a radius of curvature of 10.7 mm. and an inner concave surface 58 with a radius of curvature of 7.8 mm. With this configuration, the lens 12 provides about 2.5 power magnification of the fundus of a normal emmotropic eye.

As is also shown in FIG. 7, the ring 54 and mushroom member 52 are fabricated so that the angle between the tip of the fibers 14 and the axis of the lens 12 in the vicinity where the fibers contact the cornea is 30°. This angle has been found to be very satisfactory; however, as is apparent, some deviation from this angle is possible. It has been found that this deviation should not exceed plus or minus 5°. Thus, the permissible range for the angle between the tip of fibers 14 and the axis of lens 12 is 25°-35°.

Ophthalmoscopes constructed in accordance with the foregoing teachings have been utilized in various tests taken in conjunction with a camera. The focusing is obtained by the camera objective, and the field lens is utilized to adjust the magnification and field of view. The image seen through the wide-angle system of ophthalmoscope 10 by either an observer or a camera is clear, sharp and bright. In fact, the serial image is bright enough to photograph with panchromatic plus film (32 ASA) at 1/30 of a second with a lens set at f 11.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An ophthalmoscope comprising a lens through which the interior of an eye can be viewed and a plurality of light-guiding optical fibers positioned in relationship to said lens so as to form a circular pattern of fibers around said lens, said fibers being positioned in relationship to said lens to prevent said fibers from intruding into the solid angle of the image of the retina from the posterior pole to the equator and with the tips of said fibers that face a patient when the ophthalmoscope is in use forming a ring of a pre-determined radius, said pre-determined radius of said ring formed by said tips and the positioning of said fibers in relationship to said lens being calculated to maximize the illumination of the interior of an eye with light traveling through said fibers, prevent blockage of an image of the interior of an eye seen by a viewer when looking through said lens and reduce the amount of reflection of the image of said fiber tips caused by the crystalline lens of the eye being viewed to enable an observer to view a retina from the posterior pole to the equator as a single image.

2. The ophthalmoscope as set forth in claim 1 wherein said lens has a configuration which enables it to be placed on a human cornea.

3. The ophthalmoscope as set forth in claim 2 wherein said ring formed by said tips is capable of contacting a cornea when the ophthalmoscope is in use.

4. The ophthalmoscope as set forth in claim 3 also including a light source connected to said fibers for illuminating the interior of an eye when the ophthalmoscope is in use.

5. The ophthalmoscope as set forth in claim 1 wherein said lens is formed of a glass having a refractive index which is at least 1.96.

6. The ophthalmoscope as set forth in claim 1 wherein the inside radius of said ring formed by said tips is 4 mms.

7. The ophthalmoscope as set forth in claim 1 wherein the tips of said fibers that face a cornea when the ophthalmoscope is in use form an angle of 30° with the axis of the lens.

8. The ophthalmoscope as set forth in claim 1 wherein the tips of said fibers that face a cornea when the ophthalmoscope is in use form an angle within the range of 25°-35° with the axis of the lens.

9. The ophthalmoscope as set forth in claim 1 wherein said fibers have a numerical aperture which is at least 0.86.

10. The ophthalmoscope as set forth in claim 1 wherein said fibers have a total effective acceptance angle which is at least 82°.

11. The ophthalmoscope as set forth in claim 1 wherein said lens has a mushroom configuration and is surrounded by an external ring member, and wherein said optical fibers are sandwiched between said lens and said external ring member, the assembly formed by said lens and said external ring member having the configuration of a contact lens.

12. The ophthalmoscope as set forth in claim 1 wherein the inside radius of said ring formed by said tips is between the range of 3.6 mm to 4 mm.

13. An ophthalmoscope comprising
   A. a contact lens
      (1) for placement contiguous with a subject's eye for viewing the interior thereof,
      (2) said lens when so placed having a field of view including at least the entirety of such subject's retina from the posterior pole to the equator, and
   B. plural light-guiding optical fibers
      (1) each having first and second end facets,
      (2) said fibers being affixed to said lens with said first facets in a circular array concentric with said lens and facing in the direction of such viewing through said lens for the illumination of such subject's eye, with light exiting from said first facet,
      (3) said fibers being disposed with both the array diameter and the fiber extensions from said first facets being so configured that light exiting from said first facets produces a field of illumination which includes at least said field of view of said lens and which is substantially free, within said field of view of said lens, of reflections thereof by the crystalline lens of such subject's eye.

14. A fundus camera comprising a first lens through which the interior of an eye can be photographed and a plurality of light-guiding optical fibers positioned in relationship to said lens so as to form a circular pattern of fibers around said lens, said fibers being positioned in relationship to said lens to prevent said fibers from intruding into the solid angle of the image of the retina from the posterior pole to the equator and with the tips of said fibers that face a patient when the camera is in use forming a ring of a predetermined radius, said predetermined radius of said ring formed by said tips and the positioning of said fibers in relationship to said lens being calculated to maximize the illumination of the interior of an eye with light traveling through said fibers, prevent blockage of an image of the interior of an eye to be photographed through said lens and reduce the amount of reflection of the image of said fiber tips caused by the crystalline lens of the eye being photographed to enable a retina to be photographed from the posterior pole to the equator as a single image, said fundus camera also containing a field lens in optical alignment with said first lens, said field lens having an aperture equal to the cone which contains the image of the retina to be photographed.

15. The fundus camera as set forth in claim 14 wherein the field lens has a radius of at least 60 mms. and an aperture of f/1.

16. The fundus camera as set forth in claim 14 wherein said field lens is attached to said camera by a bellows.

17. The fundus camera as set forth in claim 16 wherein said first lens is formed of a glass having a refractive index which is at least 1.96.

18. The fundus camera as set forth in claim 17 wherein the inside radius of said ring formed by said tips is 4 mms.

19. The fundus camera as set forth in claim 16 wherein said fibers are positioned in relationship to said first lens so that the tips of said fibers that face a cornea when the camera is in use form an angle of 30° with the axis of said lens.

20. The fundus camera as set forth in claim 16 wherein said fibers are positioned in relationship to said first lens so that the tips of said fibers that face a cornea when the camera is in use form an angle within the range of 25°–35° with the axis of said lens.

21. The fundus camera as set forth in claim 16 wherein said fibers have a numerical aperture which is at least 0.86.

22. The fundus camera as set forth in claim 16 wherein said fibers have a total effective acceptance angle which is at least 82°.

23. The fundus camera as set forth in claim 16 wherein said first lens has a mushroom configuration and is surrounded by an external ring member, and wherein said optical fibers are sandwiched between said lens and said external ring member, the assembly formed by said lens and said external ring member having the configuration of a contact lens.

24. Device for examining an eye fundus, comprising a plurality of optical fibers the transmitting ends of which are positioned in such a way as to distribute their light beams in order to pass through the pupil and illuminate the eye fundus and an optical system suitable to form an image of the eye fundus thus lit, said device comprising means for supporting the optical fibers arranged with the general shape of a conical crown having a semi-angle at the apex comprised between 25° and 35° and along which the terminations of the optical fibers are positioned, the transmitting ends of said fibers being distributed over the smaller base of the crown, said supporting means having, fixed prependicularly to its axis, at least one lens situated in the immediate vicinity of said smaller base, the inside diameter of said smaller base and the diameter of the said lens being comprised between 7.2 and 8 mm, said smaller base being adapted to be placed in contact with the cornea.

25. Device in accordance with claim 24 wherein the said lens is divergent and spherical, the radius of curvature of the surface thereof which is nearest to the said smaller base being substantially equal to that of the cornea of the human eye.

26. Device in accordance with claim 24 characterized in that said optical system has a focal distance close to that of the human eye and is corrected for an anterior diaphragm.

27. An ophthalmic device comprising a lens through which the interior of an eye can be viewed and a plurality of light-guiding optical fibers disposed in a circular pattern around said lens, said fibers being positioned relative to said lens outside the solid angle containing the image of the retina from the posterior pole to the equator and with the tips of said fibers that face a patient when the ophthalmoscope is in use forming a ring, said fibers being arranged relative to said lens and with the tips thereof arranged in said ring for illuminating the interior of an eye from at least the posterior pole to the equator with light travelling through said fibers and for viewing through said lens said illuminated interior of the eye as a single image substantially unobstructed by the fibers and for producing said image substantially without reflections, from the crystalline lens of the eye being viewed, of illumination from the fibers.

28. An ophthalmic device according to claim 27 in which said lens includes a contact lens for placement on the cornea of the eye being viewed and the tips of said fibers form said ring for placement on that eye cornea.

29. An ophthalmic device according to claim 27 in which said ring of fiber tips has an inside radius substantially between 3.6 and 4 mm.

30. An ophthalmic device according to claim 27 in which said fibers at the tips thereof form an angle between 25° and 35° with the axis of said lens.

* * * * *